United States Patent [19]

Nikles et al.

[11] 3,944,674
[45] Mar. 16, 1976

[54] COMBATING INSECTS WITH O DIMETHOXYMETHYLPHENYL-N-METHYLCARBAMATE

[75] Inventors: Erwin Nikles, Allschwill; Volker Dittrich; Ladislaus Pinter, both of Basel, all of Switzerland

[73] Assignee: Ciba-Geigy AG, Basel, Switzerland

[22] Filed: Oct. 2, 1974

[21] Appl. No.: 511,408

Related U.S. Application Data

[60] Division of Ser. No. 199,008, Nov. 15, 1971, Pat. No. 3,856,968, which is a continuation of Ser. No. 758,616, Sept. 9, 1968, abandoned, which is a continuation-in-part of Ser. No. 647,274, April 28, 1967, abandoned, which is a division of Ser. No. 493,256, Oct. 5, 1965, abandoned.

[30] Foreign Application Priority Data

Oct. 8, 1964 Switzerland.................. 13113/64

[52] U.S. Cl..................... 424/300; 71/106
[51] Int. Cl.$^2$............................. A01N 9/20
[58] Field of Search................... 424/300

[56] References Cited

UNITED STATES PATENTS

| | | | |
|---|---|---|---|
| 3,349,115 | 10/1967 | Weil et al. ............................ | 424/277 |
| 3,470,236 | 9/1969 | Hausweiler et al. ................. | 424/300 |
| 3,829,437 | 8/1974 | Zumach et al...................... | 424/300 |

*Primary Examiner*—V. D. Turner
*Attorney, Agent, or Firm*—Frederick H. Rabin

[57] ABSTRACT o-dimethoxy methylphenyl-N-methylcarbamate is disclosed as being useful for combatting insects.

2 Claims, No Drawings

COMBATING INSECTS WITH O DIMETHOXYMETHYLPHENYL-N-METHYLCARBAMATE

This is a division of application Ser. No. 199,008, filed on Nov. 15, 1971, now U.S. Pat. No. 3,856,968, which is a continuation of application Ser. No. 758,616, filed on Sept. 9, 1968, now abandoned. Said application Ser. No. 758,616 is a continuation-in-part of application Ser. No. 647,274, filed on Apr. 28, 1967, which in turn was a division of application Ser. No. 493,256 filed on Oct. 5, 1965, both now abandoned.

The present invention provides new carbamates and processes for their manufacture as well as preparations that contain such carbamates.

The new carbamates correspond to the following general formula

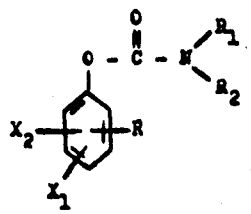

(I)

wherein $R_1$ and $R_2$ are identical or different and each represents a hydrogen atom or a lower alkyl or lower alkenyl radical: $X_1$ and $X_2$ are identical or different and each represents a hydrogen atom or a lower saturated or unsaturated aliphatic radical, a halogen atom or a nitro group, and R represents a grouping of the formula

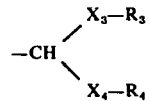

in ortho- or meta-position to the carbamoyloxy group, in which formula $X_3$ and $X_4$ are identical or different and each represents oxygen or sulphur and $R_3$ and $R_4$ are identical or different and each represents an alkyl, alkenyl or alkinyl radical or, together with the whole residue R, may form a saturated or unsaturated heterocycle having 5 t 7 members which contains $X_3$ and $X_4$ as hetero atoms, and in which $R_3$ and $R_4$ may be substituted by lower aliphatic radicals, halogen, nitro or the hydroxyl group.

The carbamates defined above possess valuable bioconal, especially insecticidal and acaricidal properties. Furthermore, these carbamates act also as herbicides, bactericides, fungicides and molluscicides.

The new carbamates of the formula (I) are obtained by reacting a phenol of the formula

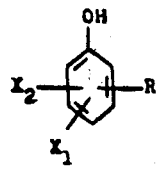

(II)

with a reactive derivative of carbonic acid and an amine of the formula

(III)

The reaction of the phenol II with a reactive derivative of carbonic acid and an amine III may be carried out in either sequence, depending to some extent on the constitution of the required final product.

According to the present process, a phenol II or an alkali metal salt thereof may be reacted, for example, with phosgene and the resulting chlorocarbonate or carbonate with an amine III.

Alternatively, the amine III may be first reacted with phosgene and the resulting carbamic acid chloride or (when $R_1$ or $R_2$ represents hydrogen) the isocyanate readily formed from it may be reacted with the phenol II. Furthermore, a urethane derived from the amine III, preferably an alkyl urethane, may be reacted with a phenol of the formula (II). (Transesterification.)

It is also possible to react an urea derived from an amine of the formula (III) with a phenol of the formula (II), preferably at raised temperature.

Some of the phenols of the formula (II) have been described in the literature, others are new. The residue R characterizes them as open-chain or cyclic acetals and mercaptals. They are manufactured by the processes known for the manufacture of this type of substance; as a rule, they are prepared by reacting an or- tho- or meta-hydroxybenzaldehyde with a lower alcohol or mercaptan in the presence of an acid catalyst, for example zinc chloride, a mineral acid or para-toluene-sulphonic acid. These reactions may also be carried out with aldehyde derivatives, for example oximes, aldehydanils, acetals (transacetalization). Another suitable route is the acetalization with the aid of orthoformic acid esters, formimine ethers, dimethylsulphite, orthosilicic acid esters in the presence of lower aliphatic alcohols, or the mercaptalization with lower orthothioborates.

Another route leading to the phenols of the formula (II) is the reaction of suitable halides with alkali metal or alkaline earth metal alcoholates and mercaptides.

The final products obtained are open-chain or cyclic acetals or mercaptals, depending on the stoichiometric proportions of the starting materials and on the valency of the alcohols or mercaptans. According to the size of the ring and the kind of hetero atom present in the residue R, the carbamates of this invention may be designated as derivatives of 1,3-dioxolan (from 1,2-glycols), of 1,3-dioxan (from 1,3-glycols), of 1,3-dioxepan (from 1,4-glycols), of 1,3-oxathiolane (from 1,2-hydroxymercaptans), of 1,3-dithiolans (from 1,2-dithiols) or of 1,3-dithians (from 1,3-dithiols).

The acetalization or mercaptalization may be performed in two stages, with the semiacetals or semi-mercaptals being formed in the first reaction stage. When different alcohols are used in the two reaction stages, mixed acetals, mercaptals or monothioacetals are obtained.

When optically active alcohols or mercaptans are used, there may be prepared optically active phenols of the formula (II) and from them optically active carbamates of the formula (I). If the residue R of the formula (I) is cyclic and substituted, further isomerizing possibilities offer themselves. A carbamate of the formula (I) whose residue R is monosubstituted may be obtained in the cis-form or trans-form. In general, the present process for the manufacture of the carbamates gives rise to mixtures of all possible isomers; these mixtures can be separated into their constituents by known methods, for example by crystallization. For the manufacture of the preparations of this invention to be used for pest control, however, the stereoisomer mixtures obtained in the manufacture of the active substances are generally used.

As alcohols and mercaptans suitable for the maufacture of the phenols of the formula (II) there may be mentioned: methanol, ethanol, propanol, isopropanol, allyl alcohol, propargyl alcohol, 2-methoxyethanol, 2-methylmercaptoethanol, 2-chloroethanol, 2-bromethanol, 2-hydroxyethanethiol, methylmercaptan, ethylmercaptan, n-propylmercaptan, isopropylmercaptan, n-butylmercaptan, allylmercaptan, chlorallylmercaptan, dichlorallylmercaptan, propargylmercaptan, 2-methoxyethanethiol, 2-methylmercaptoethanethiol, ethyleneglycol, racemic 1,2-propanediol, (+)(S)-1,2-propanediol, (−)(R)-1,2-propanediol, 3-fluoro-1,2-propanediol, 3-chloro-1,2-propanediol, 3-bromo-1,2-propanediol, 3-iodo-1,2-propanediol, 3-methoxy-1,2-propanediol, 3-ethoxy-1,2-propanediol, 3-isopropoxy-1,2-propanediol, 3-allyloxy-1,2-propanediol, 3-methallyloxy-1,2-propanediol, 3-propargyloxy-b 1,2-propanediol, 3-acetoxy-1,2-propanediol, 3-methylmercapto-1,2-propanediol, 3-chlorallylmercapto-1,2-propanediol, glycerol, 1,3-propanediol, 2-chloro-1,3-propanediol, 2-bromo-1,3-propanediol, 2-nitro-1,3-propanediol, (+)(R)-1,2-butanediol, (−)(S)-1,2-butanediol, racemic 1,2-butanediol, 1,3-butanediol, 1,4-butanediol, meso-2,3-butanediol, (−)(2R:3R)-2,3-butanediol, (+)(2S:3S)-2,3-butanediol, 1-butene-3,4-diol, 2-butene-1,4-diol, 2-hydroxymethyl-2-propen-1-ol, 2-hydroxymethyl-2-buten-1-ol, 2-methyl-1,2-propanediol, 3-chloro-2-methyl-1,2-propanediol, 3-chloro-2-chloromethyl-1,2-propanediol, 2-methyl-1,3-propanediol, 2-nitro-2-methyl-1,3-propanediol, 1,2-pentanediol, 1,3-pentanediol, 2,3-pentanediol, 2,4-pentanediol, 1-pentene-3,4-diol, 2-methyl-1,2-butanediol, 2-methyl-1,3-butanediol, 2-methyl-2,3-butanediol, 2-methyl-2,4-butanediol, 2-methyl-3,4-butanediol, 2-ethyl-1,3-propanediol, 1,4-dichloro-2-methyl-2,3-butanediol, 4-bromo-2-methyl-2,3-butanediol, 4-iodo-2-methyl-2,3-butanediol, 2,2-dimethyl-1,3-propanediol, 2,2-bischloromethyl-1,3-propanediol, 2,4-hexanediol, 2-methyl-2,3-pentanediol, 3-methyl-2,4-pentanediol, 2,2-dimethyl-3,4-butanediol, 1,5-hexadiene-3,4-diol, 1,2-ethanedithiol, 2-ethanol-1-thiol, 1,2-propanedithiol, 2-propanol-1-thiol, 3-chloro-2-propanol-1-thiol, 3-propanol-1-thiol, 1,3-propanedithiol, 1,2-butanedithiol, 2,3-butanedithiol, 2,2-dimethyl-1,3-propanedithiol or the like.

Most of the aromatic aldehydes required for the manufacture of the phenols of the formula (II) by the acetalizing or mercaptalizing method are known, while the others are new. They are obtained by the usual methods known for the manufacture of ortho- and meta-hydroxybenzaldehydes (cf. for example Houben-Weyl, Methoden der organischen Chemie, volume 7, part 1, Stuttgart 1954).

From among the suitable aldehydes there may be mentioned: Salicylaldehyde, the isomeric salicylaldehydes substituted by methyl, fluorine, chlorine, bromine, iodine, methoxy, isopropoxy, allyloxy, propargyloxy, methylmercapto, allylmercapto, chlorallylmercapto, propargylmercapto, trifluoromethyl, nitro, lower dialkylamine or dialkenylamino groups, for example 4-methyl-salicylaldehyde, 5-methyl-salicylaldehyde, 4-methoxy-salicylaldehyde, 4-isopropoxy-salicylaldehyde, 4-chloro-salicylaldehyde, 5-chloro-salicylaldehyde, 5-bromo-salicylaldehyde, 5-methyl-mercapto-salicylaldehyde, 4-trifluoromethyl-salicylaldehyde, 5-nitro-salicylaldehyde, 4-dimethylamino-salicylaldehyde, 3,5-dichloro-salicylaldehyde, 3,5-dibromo-salicylaldehyde, 3,5-dinitro-salicylaldehyde, 3-hydroxybenzaldehyde, 2-chloro-3-hydroxybenzaldehyde, 6-bromo-3-hydroxybenzaldehyde, 5-hydroxy-3-methylbenzaldehyde and the like.

As mentioned above, the new carbamates of the formula (I) obtained by the present process possess valuable biocidal properties. Inter alia, these carbamates develop a very strong action, for example, against houseflies, aphids, caterpillars and beetles, for example corn weavil and Colorado beetle. Their contact effect is far superior to that of the known active substance "Carbaryl" (N-methyl-α-naphthylcarbamate).

Accordingly, the present invention also provides pesticidal preparations containing as active ingredient at least one carbamate of the formula (I) and, if desired, one of the following additives: Vehicles, solvents, diluents, dispersants, wetting agents, adhesives, fertilizers and, if required, further pesticides.

The broad aspect of the biocidal effect of the new preparations offers the advantage that a wide variety of vegetable and animal pests can be controlled with them.

They are not only suitable for use as herbicides but, when applied in a concentration that does not produce phytotoxic effects, they may also be used in plant protection since they develop an excellent effect against harmful microorganisms, for example against fungi, for example *Alternaria solani*, *Phytopthora infestans* and *Septoria apii*, as well as against harmful insects, acarides, nematodes and their ova and larvae.

Furthermore, the new preparations may also be used quite generally as microbicides, for example against Aspergillus species.

Spray solutions of compounds of the general formula (I) may be prepared, for example, with petroleum fractions having a high to medium boiling range, for example Diesel oil or kerosene, coal tar oil, or oils of vegetable or animal origin, as well as hydrocarbons, for example alkylated naphthalenes, tetrahydronaphthalene, if desired or required with the use of xylene mixtures, cyclohexanols, ketones or chlorinated hydrocarbons for example trichloroethane or tetrachloroethane, trichloroethylene or trior tetrachlorobenzenes. It is advantageous to use organic solvents having a boiling point above 100°C.

It is especially advantageous to prepare aqueous forms of application from emulsion concentrates, pastes or wettable spray powders by addition of water. Suitable emulsifiers or dispersants are non-ionic products, for example condensation products of aliphatic alcohols, amines or carboxylic acids with a long-chain hydrocarbon residue of about 10 to 20 carbon atoms with ethylene oxide, for example the condensation product from octadecyl alcohol with 25 to 30 mols of ethylene oxide, or of commercial oleylamine with 15 mols of ethylene oxide, or of dodecylmercaptan with 12 mols of ethylene oxide. As suitable anionic emulsifiers, there may be mentioned the following: The sodium salt of dodecyl alcohol sulphuric acid ester, the sodium salt of dodecylbenzosulphonic acid, the potassium or triethanolamine salt of oleic acid or of abietic acid or of a mixture of these two acids, or the sodium salt of a petroleumsulphonic acid. Suitable cationic dispersants are quaternary ammonium compounds, for example cetyl pyridinium bromide and dihydroxyethyl benzyl dodecyl ammonium chloride.

For the manufacture of dusting and casting preparations, there may be used as solid vehicles: talcum, kaolin, bentonite, calcium carbonate, calcium phosphate or coal, cork meal, wood meal or other materials of vegetable origin. It is also very advantageous to manufacture the preparations in the form of granulates. The various forms of application may contain the conventional additives that improve the distribution, the adhesion, stability to rain or the penetration; as such substances there may be mentioned fatty acids, resin, glue, casein and alginates.

The preparations of this invention may be used by themselves or in conjunction or admixture with conventional pesticides, especially insecticides, acaricides, nematocides, bactericides, fungicides, herbicides and the like.

Especially suitable for insect control are carbamates of the formula (I) wherein $R_1$ represents a hydrogen atom and $R_2$ a lower alkyl radical, for example methyl, and R stands for a dioxolanyl, oxathiolanyl or dithiolanyl residue linked in ortho-position, and wherein $X_1$ and $X_2$ preferably represent hydrogen.

The following Examples illustrate the invention, the parts and percentages being by weight.

EXAMPLE 1 a. ortho-(1,3-dioxolan-2-yl)-phenol

A mixture of 244 parts of salicylaldehyde, 125 parts of ethyleneglycol, 1 part of zinc chloride, 1 part by volume of concentrated phosphoric acid and 500 parts by volume of benzene was boiled in a circulating distillation apparatus until water was no longer being eliminated. The solution of the product was filtered and evaporated. The residue was distilled under a high vacuum. The product boiled at 88° to 91°C under 0.04 mm Hg pressure and melted at 67° to 70°C.

b. ortho-(1,3-dioxolan-2-yl)-phenyl-N-methyl-carbamate

A solution of 50 parts of ortho-(1,3-dioxolan-2-yl)-phenol in 300 parts by volume of dry toluene was mixed with about 0.2 part by volume of triethylamine, and 20 parts of methylisocyanate were dropped into this solution at room temperature. The temperature rose gradually to 31°C. The mixture was kept for 1 day at room temperature. The product was filtered off and crystallized from toluene; it melted at 111° to 114°C.

EXAMPLE 2

When glycols (polyols) were reacted with unsubstituted or substituted ortho- or meta-hydroxybenzaldehydes, the condensation as described in Example 1 lead to cyclic acetals. When these acetals were reacted with methylisocyanate, they furnished, for example, the following carbamates:

| No. | Aldehyde | Glycol | Cyclic acetal | Carbamate |
| --- | --- | --- | --- | --- |
| 1 | salicylaldehyde | 1,2-propanediol | b.p.85°C/0.03mm Hg | ortho-(4-methyl-1,3-dioxolan-2-yl)-phenyl-N-methyl-carbamate (crystallizes gradually) |
| 2 | " | 2,3-butanediol (commercial mixture of stereoisomers) | b.p.86°C.0.07mm Hg | ortho-(4,5-dimethyl-1,3-dioxolan-2-yl)-phenyl-N-methyl-carbamate, m.p. 70 – 105°C |
| 3 | " | 1-butene-3,4-diol | b.p.82°C/0.08mm Hg | ortho-(4-vinyl-1,3-dioxolan-2-yl)-phenyl-N-methyl-carbamate |
| 4 | " | glycerol-α-monochlorohydrin | b.p.111 – 114°C 0.3mm Hg | ortho-(4-chloromethyl-1,3-dioxolan-2-yl)-phenyl-N-methyl-carbamate, m.p. about 30 to 70°C |
| 5 | " | glycerol | m.p.148 to 149°C from acetonitrile | ortho-(4-hydroxymethyl-1,3-dioxolan-2-yl)-phenyl-N-methyl-carbamate, or ortho-(5-hydroxy-1,3-dioxan-2-yl)-phenyl-N-methyl-carbamate, m.p.130 to 134°C. As by-product the corresponding bis-N-methyl-carbamate melting at 170 to 172°C was obtained. |
| 6 | " | 1,3-propanediol | b.p.92 to 96°C 0.01mm Hg | ortho-(1,3-dioxan-2-yl)-phenyl-N-methyl-carbamate. M.p.125 to 127°C (from toluene) |
| 7 | " | 1,3-butanediol | b.p.89 to 95°C 0.06mm Hg | ortho-(4-methyl-1,3-dioxan-2-yl)-phenyl-N-methyl-carbamate. M.p.146 to 148°C (from acetonitrile) |
| 8 | " | neopentylglycol | b.p.90°C/0.06mm Hg - m.p.58 – 60°C | ortho-(5,5-dimethyl-1,3-dioxan-2-yl)-phenyl-N-methyl-carbamate. M.p.122 to 124°C (from carbon tetrachloride) |
| 9 | salicylaldehyde | 3-methyl-2,4-pentandediol | b.p.93°C/0.01mm Hg | ortho-4,5,6-trimethyl-1,3-dioxan-2-yl)-phenyl-N-methyl-carbamate m.p. 118 to 136°C |
| 10 | " | 2-methyl-2-nitro-1,3-propanediol | m.p.90 to 93°C (from ether+ cyclohexane) | ortho-(5-methyl-5-nitro-1,3-dioxan-2-yl)-phenyl-N-methyl-carbamate m.p.131 – 134°C (from isopropanol) |
| 11 | " | 2-butene-1,4-diol | b.p.87°C/0.03mm Hg | ortho-(1,3-dioxep-5-en-2-yl)-phenyl-N-methyl-carbamate m.p.94 – 95°C (from toluene) |
| 12 | 4-methylsalicyl-aldehyde | ethyleneglycol | b.p.98°C/0.02mm Hg; crystallizes | ortho-(1,3-dioxolan-2-yl)-meta'-methylphenyl-N-methyl-carbamate m.p.96 to 99°C (from toluene) |
| 13 | 5-methylsalicyl-aldehyde | " | b.p.95 – 96°C 0.01mm Hg | ortho-(1,3-dioxolan-2-yl)-para-methylphenyl-N-methyl-carbamate m.p.104 to 106°C (from carbon tetrachloride) |
| 14 | mixture of 4- and 6-trifluoro-methyl-salicyl-aldehyde +) | 1,2-propanediol | b.p.90°C/0.7mm Hg | ortho-(4-methyl-1,3-dioxolan-2-yl)-meta- and meta'-trifluoromethylphenyl-N-methyl carbamate (viscous oil) |
| 15 | 5-chlorosalicyl- | ethyleneglycol | m.p.82°C (from | para-chloro-ortho-(1,3-dioxolan-2-yl)-phenyl- |

-continued

| No. | Aldehyde | Glycol | Cyclic acetal | Carbamate |
|---|---|---|---|---|
| | aldehyde | | toluene) | N-methyl carbamate m.p.109 – 112°C (from benzene+hexane) |
| 16 | mixture of 4- and 6-chlorosalicyl-aldehyde | 1,2-propanediol | b.p.93 – 98°C/0.01mm Hg | ortho-(4-methyl-1,3-dioxolan-2-yl)-meta- and meta'-chlorophenyl-N-methyl carbamate, m.p. about 90 to 100°C |
| 17 | 5-bromosalicyl-aldehyde | ethyleneglycol | m.p.81°C (from hexane) | para-bromo-ortho-(1,3-dioxolan-2-yl)-phenyl-N-methyl-carbamate, m.p. 107 to 109°C (from ethylene chloride) |
| 18 | 3,5-dibromo-salicyl-aldehyde | '' | b.p.145°C/0.17mm Hg m.p.60 to 64°C | ortho,para-dibromo-ortho'-(1,3-dioxolan-2-yl)-phenyl-N-methyl-carbamate m.p.135 – 139°C (from acetonitrile) |
| 19 | 3,5-dinitro-salicylaldehyde | '' | m.p. 134 – 140°C (from chlorobenzene) | ortho,para-dinitro-ortho'-(1,3-dioxolan-2-yl)-phenyl-N-methyl-carbamate m.p.149 – 155°C (from acetone) |
| 20 | meta-hydroxy-benzaldehyde | '' | b.p.113 to 115°C/0.03 mm Hg | meta-(1,3-dioxolan-2-yl)-phenyl-N-methyl-carbamate, m.p.73 to 77°C (from toluene) |
| 21 | meta-hydroxy-benzaldehyde | 2,3-butanediol (commercial) | b.p.115°C/0.1mm Hg | meta-(4,5-dimethyl-1,3-dioxolan-2-yl) phenyl-N-methyl-carbamate, viscous oil |

+) 4(6)-trifluoromethyl-salicylaldehyde can be prepared from 3-trifluoromethylphenol by the method of J.C.Duff [J.Chem.Soc.1941, page 547, Proc.Iowa Acad.Sci.52, page 191 (1954)]. It boils at 77 to 80°C under 14mm Hg pressure.

EXAMPLE 3

Salicylaldehyde diethyl acetal

A mixture of 122 parts of salicylaldehyde, 180 parts of orthoformic acid ethyl ester and 120 parts of anhydrous ethanol was mixed with 1 ml of concentrated hydrochloric acid, whereupon the whole heated up spontaneously. After a short time, the solution was heated to the boil and then evaporated under vacuum, and the residue distilled under a high vacuum. The product passed over at 80°C under 0.15 mm Hg pressure.

ortho-(diethoxymethyl)-phenyl-N-methyl-carbamate

A solution of 138 parts of salicylaldehyde diethyl acetal, 46 parts of methylisocyanate and 0.5 part of triethylenediamine in 1,000 parts by volume of dry toluene was kept for 14 hours at room temperature. The resulting crystalline ortho-(diethoxymethyl)-phenyl-N-methyl-carbamate was filtered off, washed with 250 parts by volume of dry toluene and dried under vacuum. It melted at 92° to 93°C.

ortho-(Dimethoxymethyl)-phenyl-N-methyl-carbamate, melting at 62° to 64°C (after crystallization from dibutyl ether), was prepared in a similar manner, starting from salicylaldehyde dimethylacetal.

EXAMPLE 4 meta-hydroxybenzaldehyde-dimethylmercaptal

122 Parts of meta-hydroxybenzaldehyde were added portion-wise at about 0°C to a mixture of 100 parts of methylmercaptan, 2 parts by volume of concentrated hydrochloric acid and 500 parts by volume of chloroform. The solution was then kept for 14 hours at room temperature and washed with potassium bicarbonate solution and with water until the washings run neutral. Evaporation of the solvent under vacuum furnished meta-hydroxybenzaldehyde dimethylmercaptal as residue. The product passed over only in very small amounts under a high vacuum.

meta-(dimethylmercapto-methyl)-phenyl-N-methyl-carbamate

81 Parts of crude meta-hydroxybenzaldehyde dimethylmercaptal and 0.4 part of triethylenediamine were dissolved in 200 parts by volume of dry ether. 29 Parts of methylisocyanate were dropped into this solution and the temperature maintained by cooling below 35°C. The mixture was left for 1 day at room temperature and then evaporated. The residue was crystallized from methanol at −10°C; the product melted at 70°C.

EXAMPLE 5

When salicylaldehyde or a substitution product thereof was condensed with a mercaptan as described in Example 4, there was obtained a mercaptal which on condensation with methylisocyanate gave rise to a carbamate. In this manner the following carbamates were accessible:

| No. | Aldehyde | Mercaptan | Mercaptal | Carbamate +) |
|---|---|---|---|---|
| 1 | salicylaldehyde | methylmercaptan | non-distilling oil | ortho-(dimethylmercapto-methyl)-phenyl-N-methyl-carbamate |
| 2 | '' | ethylmercaptan | '' | ortho-(diethylmercapto-methyl)-phenyl-N-methyl-carbamate m.p.41 – 45°C |
| 3 | '' | isopropylmercaptan | '' | ortho-(diisopropylmercapto-methyl)-phenyl-N-methyl-carbamate |
| 4 | '' | allylmercaptan | '' | ortho-(diallylmercapto-methyl)-phenyl-N-methyl-carbamate |
| 5 | '' | propargyl-mercaptan | '' | ortho-(dipropargylmercapto-methyl)-phenyl-N-methyl-carbamate |
| 6 | '' | n-butyl-mercaptan | '' | ortho-(di-n-butylmercapto-methyl)-phenyl-N-methyl-carbamate |
| 7 | 5-bromo-salicyl-aldehyde | methylmercaptan | '' | para-bromo-ortho-(dimethylmercapto-methyl)-phenyl-N-methyl-carbamate m.p.83 – 85°C (from methanol) |
| 8 | 3-methoxy-salicyaldehyde | '' | '' | ortho'-methoxy-ortho-(dimethylmercapto-methyl)-phenyl-N-methyl-carbamate m.p.90 – 91°C |
| 9 | 3,5-dinitro-salicylaldehyde | '' | m.p.79 – 80°C (from methanol) | ortho',para-dinitro-ortho-(dimethyl-mercapto-methyl)-phenyl-N-methyl-carbamate |

| No. | Aldehyde | Mercaptan | Mercaptal | Carbamate +) |
|-----|----------|-----------|-----------|--------------|
| | | | | m.p.185°C, depending on the heating speed (from acetonitrile) |

+) The carbamates, which are only obtained in the form of oils, are identified by their elementary analyses

EXAMPLE 6 ortho-[Bis(2-hydroxyethylmercapto)-methyl]-phenol

61 Parts of salicylaldehyde were stirred into an ice-cooled mixture of 150 parts of 2-mercaptoethanol and 10 parts by volume of concentrated hydrochloric acid. The batch was then stirred for 1 hour at room temperature, extracted with 2 × 200 parts by volume of chloroform, the product was dissolved in ether and washed with 2 × 250 parts by volume of cold-saturated potassium bicarbonate solution. The solution was dried over anhydrous sodium sulphate, filtered, evaporated and freed from the last remnants of solvent under a high vacuum. The highly viscous residue was pure ortho-[bis-(2-hydroxyethylmercapto)-methyl]-phenol.

ortho-[Bis-(2-hydroxyethylmercapto)-methyl]-phenyl-N-methyl carbamate

39 Parts of the above mercaptal were dissolved in 250 parts by volume of dry ether, and 0.2 part of triethylenediamine and 9.5 parts of methylisocyanate were added. The temperature of the solution rose and the carbamate formed settled out in the form of an oil; it was freed under a high vacuum from the last remnants of solvent.

EXAMPLE 7 ortho-(ethylmercapto-methylmercapto-methyl)-phenol

48 Parts of methylmercaptan were mixed with 122 parts of salicylaldehyde while cooling with ice. The mixture was then kept for 1 hour at room temperature and then added in portions to 62 parts of ethylmercaptan containing 2 parts by volume of concentrated hydrochloric acid, while cooling with ice. The product was again kept at room temperature, then diluted with ether and washed with bicarbonate solution until free from acid. The solution was dried over anhydrous sodium sulphate, filtered and evaporated.

ortho-(ethylmercapto-methylmercapto-methyl)-phenyl-N-methyl-carbamate

64 Parts of the above mercaptal were reacted at room temperature in 200 parts by volume of dry toluene in the presence of 0.2 part of triethylenediamine with 20 parts of methylisocyanate. After 14 hours' reaction time, the solution was evaporated. The residue was dissolved in toluene, and, while being cooled with ice, was washed with 2 × 100 parts by volume of 2N-sodium hydroxide solution and then with 50 parts by volume of molar monosodium phosphate solution, dried and evaporated. The carbamate formed was obtained in the form of an oil.

EXAMPLE 8 ortho-(1,3-oxathiolan-2-yl)-phenol

82 Parts of 2-mercaptoethanol were mixed with 0.5 part by volume of concentrated hydrochloric acid and then dropwise with 122 parts of salicylaldehyde; the temperature of the mixture rose. The reaction mixture was stirred for 1 hour at room temperature, then diluted with 500 parts by volume of ether and washed with sodium bicarbonate solution and then with water until the washings ran neutral. The solution was dried over anhydrous sodium sulphate, filtered and evaporated.

The viscous residue was heated under a high vacuum at a bath temperature of 160°C, and the volatile phase was condensed. The condensate was then fractionated. At 112°C under a pressure of 0.05mm Hg, the ortho-(1,3-oxathiolan-2-yl)-phenol formed passed over and crystallized on standing. It melted at 72° – 74°C.

ortho-(1,3-oxathiolan-2-yl)-phenyl-N-methyl-carbamate

15 Parts of methylisocyanate and 0.1 part of triethylenediamine were added to a solution of 37 parts of ortho-(1,3-oxathiolan-2-yl)-phenol in 100 parts by volume of dry toluene. The mixture was moderately cooled to mantain its temperature below 35°C. After a few hours, the resulting crystalline product was filtered off and recrystallized from toluene or carbon tetrachloride. It melted at 108° to 109°C.

EXAMPLE 9 ortho-(1,3-dithiolan-2-yl)-phenol

A mixture of 10.4 parts of ethanedithiol and 12.2 parts of salicylaldehyde was mixed with 0.1 part of concentrated hydrochloric acid, whereupon the temperature rose considerably. The reaction product was dissolved in 100 parts by volume of toluene and washed with sodium bicarbonate solution and then with water until the washings ran neutral. The solution was dried over anhydrous sodium sulphate, filtered and evaporated. The residue was distilled under a high vacuum. It boiled at 129°C under 0.12mm Hg pressure.

ortho-(1,3-dithiolan-2-yl)-phenyl-N-methyl-carbamate ortho-(1,3-dithiolan-2-yl)-phenol was reacted with methylisocyanate in toluene in -Dithiolan-presence of a catalytic quantity of triethylenediamine as described in the preceding Examples. The product was obtained in crystalline form, and melted at 129° to 132°C.

The pure carbamate, obtained by crystallization from acetonitrile, melted at 139°C.

In a similar manner, the following are prepared:

ortho-(1,3-dithian-2-yl)-phenyl-N-methyl-carbamate, melting at 155° to 157°C; from ortho-(1,3-dithian-2-yl)-phenol melting at 132° to 133°C.

meta-(1,3-dithiolan-2-yl)-phenyl-N-methyl-carbamate, melting at 93° to 96°C; from meta-(1,3-dithiolan-2-yl)-phenol (an oil of which only small amounts can be distilled at 110°C bath temperature under a high vacuum).

ortho-(4-methyl-1,3-dithiolan-2-yl)-phenyl-N-methyl-carbamate.

ortho-(4-hydroxymethyl-1,3-dithiolan-2-yl)-phenyl-N-methyl-carbamate, a resinous mass from ortho-(4- hydroxymethyl-1,3-dithiolan-2-yl)-phenol (prepared from salicylaldehyde and 2,3-dimercapto-1-propanol).

EXAMPLE 10 ortho,para-dinitro-ortho'-(1,3-dioxolan-2-yl)-phenol

A mixture of 196 parts of 3,5-dinitrosalicylaldehyde, 70 parts of glycol and 500 parts by volume of benzene was boiled in the presence of 1 part of anhydrous zinc chloride and 1 part by volume of concentrated phosphoric acid in a circulation distillation apparatus, until water was no longer being eliminated. After cooling, the product were filtered off and crystallized from chlorobenzene; it melted at 134° to 140°C.

ortho,para-dinitro-ortho'-(1,3-dioxolan-2-yl)-phenyl-N,N-dimethyl-carbamate 11.3 Parts of dimethylcarbamic acid chloride were added to a mixture of 25.6 parts of ortho,para-dinitro-ortho'-(1,3-dioxolan-2-yl)-phenol, 200 parts by volume of chlorobenzene and 25 parts of triethylamine. The solution was heated for 5 hours at 130°C, allowed to cool, filtered, washed with 2N-sodium carbonate solution and evaporated. The residue was crystallized from alcohol. The product melted at 141° to 142°C.

By a similar reaction of ortho-(dimethylmercaptomethyl)-phenol with dimethylcarbamic acid chloride in boiling dioxane, washing the product with 2N-sodium hydroxide solution, there was obtained ortho-(dimethylmercaptomethyl)-phenyl-N,N-dimethyl-carbamate. On distillation under a high vacuum, a small amount of this product was obtained as a colourless, viscous oil.

EXAMPLE 11

Dusting Agent

Equal parts of an active substance described in Examples 1 to 10 were mixed with precipitated silica and finely ground. When this powder is mixed with kaolin or talcum, it may be used in the form of dusting preparations having the desired concentration of active substance. In general, preparations containing 1 to 5% of active substance are preferred.

Spray Powder

To manufacture a spray powder, the following ingredients, for example, were mixed and then finely ground:
50 parts of an active substance of Examples 1 to 10
20 parts of Hisil (highly adsorbent, precipitated silica)
25 parts of bolus alba (kaolin)
3.5 parts of a reaction product from para-tertiary octylphenol and ethylene oxide
1.5 parts of sodium 1-benzyl-2-stearyl-benzimidazole-6,3'-disulphonate.

Emulsion Concentrate

Readily soluble active substances were also formulated in the form of an emulsion concentrate as follows:
20 parts of active substance
70 parts of xylene
10 parts of a mixture of a reaction product of an alkylphenol with ethylene oxide and calcium dodecyl benzene-sulphonate
were mixed. On dilution with water to the desired concentration, an emulsion suitable for spraying was obtained.

EXAMPLE 12

The active substance of Example 1 and the active substance "Carbaryl" were subjected to a comparative test to establish their contact effect against houseflies and corn weavils. The new substance displayed a much greater, distinct contact-insecticidal effect.

When applied in a concentration of 0.04% in the control of aphids (aphis fabae) on young bean plants, it was found that after 2 days the active substance of Example 1 had completely destroyed the aphids. It was found to have a good diffusion and distinct systemic effect.

Carbaryl was found to be ineffective in these tests. Carbaryl has the composition of 1-naphthyl-N-methyl-carbamate.

The above-mentioned active substance is active in limit concentrations of 1.2 parts per million against aedes larvae (24 hours).

The compound was also tested in dust form against various pests (1%, 2g/m² = 20kg per hectare) and the following results were recorded:

|  | after 6 hours | after 24 hours |
|---|---|---|
| Periplaneta americana | 100% |  |
| Phyllodronia germanica | 100% |  |
| Porcellio scaber | 100% |  |
| Formica rufa |  | 100% |

A topical test on larvae of Periplaneta americana revealed in an evaluation made 24 hours later the following limit concentration of active substance compared with various commercially available phosphoric acid esters:

Phosphoric acid ester I        6
Phosphoric acid ester II       13    in γ per pest
Phosphoric acid ester III       9
active substance of
Example 12
I   = O,O-dimethyl-O-(3-methyl-4-nitrophenyl)-thionophosphate
II  = O,O-dimethyl-O-(1-chloro-1-N-diethyl-carbaminyl-1-propen-2-yl)-phosphate
III = O,O-dimethyl-O-(4-methylmercapto-3-methyl-phenyl)-thinophosphate.

The active substance of Example 1 acts also against spider mites (Tetranychus urticae).

When tested as a stomach poison on Carausius, the said active substance displayed a good effect, against Prodenia a moderate to good effect and against Gastroidea rather a good effect.

EXAMPLE 13

The active substance ortho-(1,3-dithiolan-2-yl)-phenyl-N-methylcarbamate was formulated as a spray powder according to Example 11 and tested as a contact pesticide against potato beetle (Leptinotarsa decemlineata) and against aphids (Hyalopterus arundinis) on plums. The exact test conditions and the results (mortality of pests tested in %) are shown in the following Table:

| Concentration of active substance | Leptinotarea decemlineata | | Hyalopterus arundinis | |
|---|---|---|---|---|
| | larvae | beetles | | |
| | result inspected after | | | |
| | 5 days | 5 days | 2 days | 5 days |
| | motality in percent | | | |
| 0.08% | 100 | 100 | 100 | 100 |
| 0.02% | 100 | 100 | 100 | 100 |
| 0.005% | 100 | 80 | 100 | 100 |
| 0.001% | — | 20 | 100 | 100 |
| 0.0003% | — | — | 100 | 80 |

What is claimed is:

1. A composition for combating insects comprising (1) as active ingredient an insecticidally effective amount of 0-dimethoymethylphenyl-N-methyl-carbamate and (2) a suitable carrier.

2. A method for controlling insects which comprises applying thereto an insecticidally effective amount of 0-dimethoxy methylphenyl-N-methylcarbamate.

\* \* \* \* \*

UNITED STATES PATENT OFFICE
CERTIFICATE OF CORRECTION

Patent No. 3,944,674   Dated March 16, 1976

Inventor(s) Erwin Nikles et al.

It is certified that error appears in the above-identified patent and that said Letters Patent are hereby corrected as shown below:

Claim 1, column 14, line 4 should read:

"amount of O-dimethoxymethylphenyl-N-methyl-"

Signed and Sealed this eighth Day of June 1976

[SEAL]

Attest:

RUTH C. MASON
*Attesting Officer*

C. MARSHALL DANN
*Commissioner of Patents and Trademarks*